(12) United States Patent
Peterson

(10) Patent No.: US 6,324,924 B1
(45) Date of Patent: Dec. 4, 2001

(54) SAMPLING SYSTEM INCLUDING A SAMPLE ADDITIVE MIXING FEATURE

(76) Inventor: Roger Peterson, Drawer 567, County Rd. 375, Old Ocean, TX (US) 77463

( * ) Notice: Subject to any disclaimer, the term of this patent is extended or adjusted under 35 U.S.C. 154(b) by 0 days.

(21) Appl. No.: 09/287,027

(22) Filed: Apr. 6, 1999

(51) Int. Cl.[7] ....................................................... G01N 1/00
(52) U.S. Cl. ................................................. 73/864; 73/863
(58) Field of Search ............................... 73/863, 864, 865, 73/61, 422 R, 865.5, 422, 423; 222/56; 366/274, 273; 356/335, 336

(56) References Cited

U.S. PATENT DOCUMENTS

| | | | |
|---|---|---|---|
| 3,747,412 | * | 7/1973 | Jones ................................... 73/423 A |
| 3,901,653 | * | 8/1975 | Jones et al. ......................... 73/422 R |
| 3,972,683 | * | 8/1976 | Lape ..................................... 73/425.6 |
| 4,069,711 | * | 1/1978 | Muschelknautz et al. ........... 73/61.4 |
| 4,532,813 | * | 8/1985 | Rinehart ............................. 73/863.02 |
| 5,001,939 | * | 3/1991 | Follett ................................ 73/864.81 |
| 5,007,297 | * | 4/1991 | Sommer ............................... 73/865.5 |
| 5,247,842 | * | 9/1993 | Kaufman et al. .................... 73/865.5 |
| 5,316,180 | * | 5/1994 | Cleland ..................................... 222/56 |
| 5,501,113 | * | 3/1996 | Harrison et al. .................... 73/865.5 |
| 6,060,320 | * | 5/2000 | Dorenkett et al. ................ 73/864.15 |

* cited by examiner

*Primary Examiner*—Daniel S. Larkin
*Assistant Examiner*—Katina Wilson
(74) *Attorney, Agent, or Firm*—Thomason, Moser & Patterson, L.L.P

(57) ABSTRACT

The present disclosure sets out a sample measuring loop connected to a valve system. The valve system connects also to a sample additive loop. The valve system connects to a sample source and an additive source. They fill the loops. The valve system connects also to a wash fluid and gas source to clear the loops and valves to enable measured mixing and delivery to a sample analyzer.

19 Claims, 7 Drawing Sheets

SAMPLING SYSTEM INCLUDING A SAMPLE ADDITIVE MIXING FEATURE

BACKGROUND OF THE INVENTION

This disclosure is directed to a sample collection system. It is a sample collection system which adds a selected flowing additive to the sample. Several examples of this are given below. Briefly, the first example will involve a water soluble sample mixed with a water based additive. This will be denoted below as W/W where the sample is first and the additive is listed second. More will be noted concerning that in the representative examples given. The second type of situation will involve an organic sample. The additive itself will be organic, and that will be denoted as O/O. The third example will involve a water based or derived sample with an oil based additive. That will be denoted as W/O. The fourth example is a reverse of the latter which will be denoted as O/W.

In the four procedures exemplified above (but not yet fully explained), there is the possibility that the sample, after mixing with the additive, will become somewhat more soluble or insoluble depending on the circumstance. This will be denoted by adding a last symbol where S represent soluble, and U represents unsoluable. As will be understood, there are degrees or variable amounts of solubility in a situation. The terms, therefore, are somewhat relative, and they simply compare soluble versus insoluble samples in a general or global fashion, not in a specific, measured, or categorical situation.

Consider for the moment the source of the sample. It can be any kind of manufacturing or processing procedure which generates the sample in some kind of carrier. It is not uncommon for this sample to be a partially completed product made by manufacturing process. Where ever it is delivered, it is delivered in the fashion or form of a flowing sample mixed in the carrier, and the carrier typically or commonly is the water or oil based carrier. While there are selected compounds which define such a water or oil based carrier, that itself can vary widely. Some solutions or carriers may have some of the attributes of water and some of the attributes of an oil based solution. Again, these are relatively loose terms and are used in a relative, not absolute sense. Suffice it to say, whether it is a precisely defined or loosely defined oil or water solvent, it flows in the system which is tied to the source or the process involved at the source.

Consider now, several different possibilities. Assume for example that the process provides a material which needs to be marked. The system delivers a sample additive. Typical additives include coloring agents or radioactive isotope tracers. Others include chelating agents and the like. All of these can be added. In some instances, it may be appropriate to just simply add a solvent which functions as a dilution medium. There are several different aspects of that. The several aspects of the dilution addition are noted below.

Consider the wide range of ratios that can be implemented. In some instances, the process sample may be quite strong and robust, thereby suggesting a measure of dilution to 1:10 or perhaps 1:100. In another instance, it may work in the opposite directions so that the process material is provided only as trace where the ratio is 100:1. The mixing ratio can be over a wide range so that the additive combined with the sample is markedly different in terms of ratio.

Without regard to the ratio, the process sample and the additive are mixed with it in a mixing chamber. They are input sequentially into a measured sample loop and additive loop. These define the respective ratios because they are measured in terms of calculated sizes. The calculated sizes enable the materials to be accumulated for the moment, and then transferred. Effectively, the present system contemplates forming measured portions of the sample and the additive.

The present system thus accomplishes mixing which is assisted by mechanical stirring. The stirring device is a flow of inactive gas. By inactive, that term is being applied to nitrogen which is effectively an inert gas. It is fair to say that it is not precisely inert in a chemical sense compared to helium, argon, etc. Nevertheless, it is cheaper than those classic inert gases and can be used for stirring purposes. Stirring is accomplished by bubbling a flow of gas through the equipment.

After stirring to achieve mixing, the system delivers the mixed sample and sample additive for delivery to an external analyzer or test instrument. Any number of external measurement instruments can be used. Any number can be effectively connected to the present system. The mixed sample and additive that are delivered are sometimes mixed so that the O/W and W/O mixtures are dissolved or simply mixed as an emulsion. The degree or extend to which mixing is accomplished is somewhat dependent on the nature of the respective two fluids making up the mixture. There are situations in which the two components making up the mixtures are able to dissolve one into the other, i.e. they go into solution. There are other instances where they do not form a solution they simply form an emulsion. Dependent on the test equipment down stream, this may be quite desirable.

A procedure of operation is also set forth. One important aspect of the present invention is that a wash cycle is included as needed. The wash cycle clears the lines between cycles of operation. For instance, this equipment can be used to make a test sample once per hour, once per day, etc. Each test sample is segregated so that it does not commingle with the earlier or later samples. That is accomplished by clearing the lines of the equipment. That is done by delivery of a wash fluid. Commonly, water is the most prevalent wash fluid. After the water is pumped through the system for a specified interval, or at least selected portions of the system, the system is dried by flowing a dry gas through it. Again, nitrogen is the preferred dry gas.

In summary, the present apparatus comprises a ten port valve which operates at two positions. The valve defines with appropriate connections a sample storage loop and an additive storage loop. They are sized as required. When operated to one position, the measured quantities are collected and stored, and then they are output to the mixing chamber for subsequent mixing.

In an alternative form, the ten port, two position single sample valve can be replaced with two separate six port valves. Variations in the valving for use with the equipment can be implemented.

BRIEF DESCRIPTION OF THE DRAWINGS

So that the manner in which the above recited features, advantages and objects of the present invention are attained can be understood in detail, more particular description of the invention, briefly summarized above, may be had by reference to the embodiments thereof which are illustrated in the appended drawings.

It is to be noted, however, that the appended drawings illustrate only typical embodiments of the invention and are therefore not to be considered limiting of its scope, for the invention may admit to other equally effective embodiments.

DETAILED DESCRIPTION OF THE PREFERRED EMBODIMENT

Figure 1:
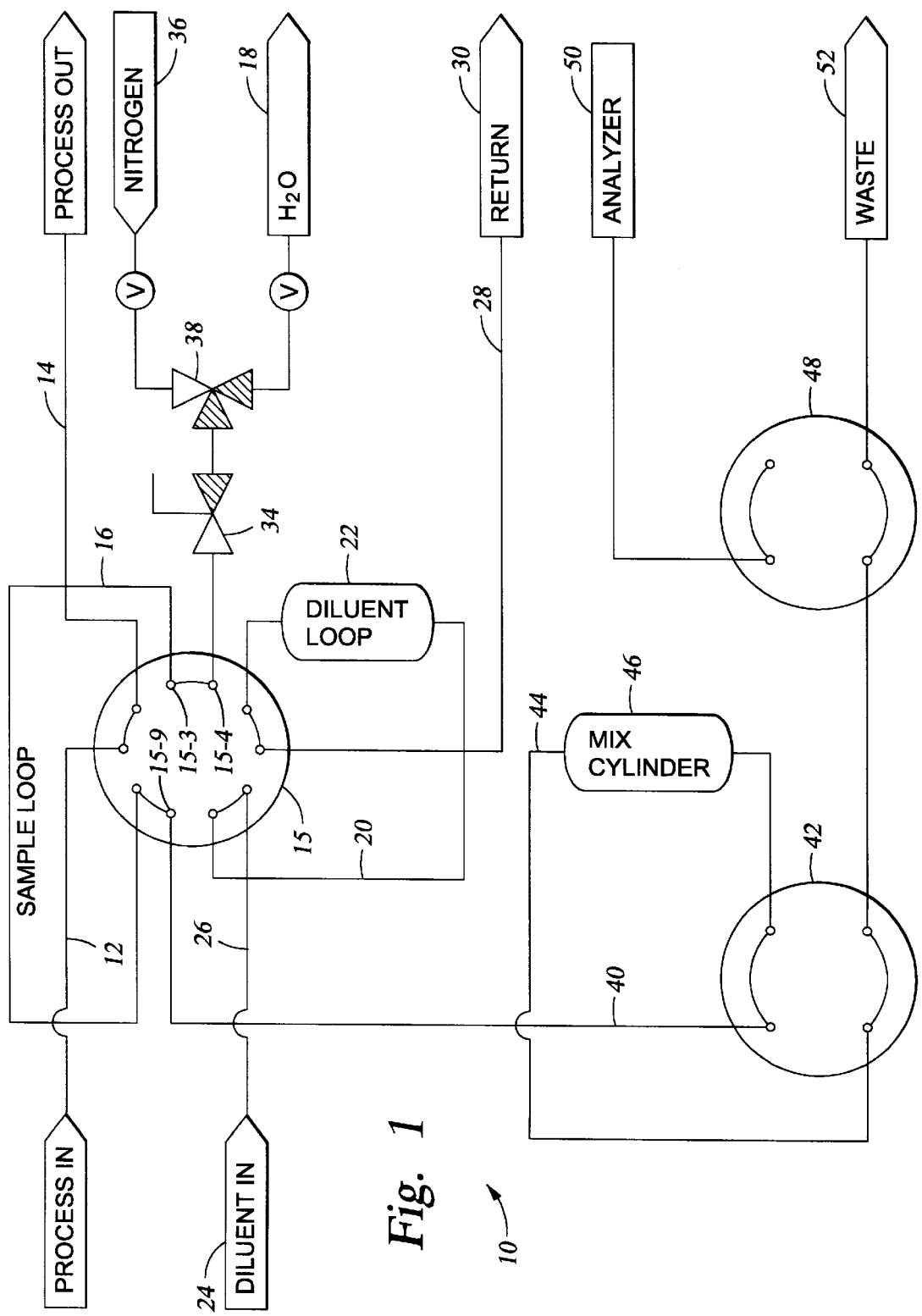
FIGS. 1 through 5 all shows the same apparatus, but illustrated in different positions to show the sequential flow of sample and sample additive fluids through the system in cooperation with a wash source, gas flow, and enabling delivery of a mixed sample with additive to a selected test instrument.

Attention is now directed to FIG. 1 of the drawings where the numeral 10 identifies the test apparatus of the present disclosure. It will be described in the context of actual use and operation. In that context, it is connected with some suitable process, thereby obtaining a sample which flows from the process. As will be understood, the nature and quality of the process can vary widely. Practically any sort of process can be connected to the equipment. This can include a process which operates at an elevated temperature or at an elevated pressure. In general terms, the process delivers a fluid flow, often a liquid, but sometimes a gas which is held at high pressure by the process operating parameters and it is input for subsequent measurement, commingling with the sample additive, and subsequent testing. For purposes of description, it will be assumed that the process furnishes a liquid and that the liquid is at some elevated pressure and some elevated temperature. Commonly, the pressure and temperature are both elevated and more or less stable at that condition.

The present system thus includes the connection through the process feedline 12 which is input from the process as noted, thereby delivering the sample feed at the process determined pressure and temperature. If need be, these can be dropped to a lower pressure or lower temperature by virtue of an intervening pressure or temperature regulator. Pressure regulators can be put in the line 12, and the line 12 can also be input through a heat exchanger which stabilizes the temperature at some lower or higher value. The line 12 is the feedline to the system while the process feed in excess of the amount required is delivered out through the line 14. It will be observed that both the lines 12 and 14 are connected to adjacent ports in the valve 15. This is the control valve, and a common embodiment that is effective for this system is a ten port rotary valve having two positions. As the description will continue, the position of the valve will be switched, the position shown in FIG. 1 being the first or initial position. No sample is taken when it is in this position. The ports of the valve will be discussed in conjunction with their connections. Thus, the process feedline 12 is uniquely correlated to a single port, and it is sometimes connected to the process outlet line as illustrated. Continuing, however, with the description, the system utilizes a measured size sample loop 16. The loop 16 is connected to the third port which will be denoted with the reference numeral 15-3. This nomenclature for the ports recognizes the ports in sequence proceeding from the first port which is connected to the sample feedline 12. The port 15-4 is connected to a pair of wash or cleaning sources. More specifically, the numeral 18 identifies a source of wash fluid, which is in this instance water. It is supplied to the system for purposes which will be described.

Another component connected to the valve 15 is the additive loop 20. Typically, it has a larger volume. It includes the serially connected loop 20 as well as the container 22 of larger size. The summation of these two components defines a volumetric measure useful in operation and will be referred to hereinafter as the additive volume. It will be defined as the volume held in the additive loop 20, that loop being augmented with the container 22 if needed. In some instances, it may not be needed at all. An additive source 24 is illustrated. The additive connects through an additive line 26 which is input to the valve 15, and that in turn cooperates with the additive loop-20. The source for the additive can be any suitable additive container such as a water tank. It can also be any other kind of additive source. To the extent that surplus additive is delivered, and it is desirable to operate in that mode, additive is pumped through the entire additive loop 20 and is delivered through an additive overflow line 28 and then to an additive storage tank 30. The tank 30 can be used to recycle additive. The tank 30 contents can be emptied back into the source 24.

As described to this juncture, both the process sample source and the additive source connect through and deliver surplus sample and additive respectively. Both are associated with loops which are metering devices. The loops can have a ratio ranging anywhere from 100:1 to 1:100. Even greater ratios can be implemented as desired. The significance of the ratios typically is determined by and related to the chemistry involved in the testing and the amount of additive that is needed. As noted, this can be dilution on the one extreme to a small trace color marker or other components which are added to the system.

Continuing with FIG. 1, the numeral 36 identifies a valued nitrogen gas source. It is pressure regulated. It is preferably dry nitrogen. It need not be perfectly pure, but it is relatively pure. When delivered, it will flow through the lines to clean out the lines. In rare cases, rather expensive inert gases such as helium and the like may be used. Commonly, nitrogen is effectively inert, although it is not inert in a technical sense. It is effectively sufficient for the purposes intended in this cleaning cycle to be described. The wash water from the source 18 is delivered through a three port, two position valve 38. In turn, that flows through a check valve 34. The check valve assures one way communication. Whether water or other liquid, the flow is from the source into the control valve 15. When the valve 38 is switched, the flow is either gas or liquid as denoted. Typically, the liquid is provided at a nominal pressure of perhaps 15 to 30 psi. By contrast, the gas may be delivered at a pressure of 50 to 150 psi. Greater gas pressures probably are not needed and would generally waste gas, and are not needed for the intended purpose.

The valved water functions as a cleaning solvent. In some instances, water may not be effective because of the hydrocarbon residue that might be left in the system. Hydrocarbon solvents are then needed, and a common one is $CCl_4$. Other solvents can be used, even including such solvents as benzene, although there are disposal difficulties which arise with some of the organic solvents.

Going back now to the valve 15, all the ports of this valve have been discussed except the valve port 15-9. That is connected to the mix line 40, that line being connected with the other valves to be discussed. The mix line 40 delivers the additive and the sample through it. That sequence will be discussed below. This flows to the mixing valve 42. This is a four port valve having two ports connected with a mix loop 44 which includes a mixing container 46. In this form, the container is a cylinder which is approximately the size of the sample and additive with some excessive capacity, perhaps best known as head room in the top part of the cylinder so that there is room for liquid agitation. If the head room is about 25% to 50% of the cylinder capacity, this is sufficient to enable bubbling through and stirring as will be described. The mix valve 42 is operated so that these are delivered into the cylinder.

FIG. 1 additionally shows a dump valve 48. It has one output which is connected with a waste container and another output connected with an analyzer 50. The waste container 52 receives the commingled sample and additive after all the system has been operated. As will be understood, some portion is delivered to the analyzer 50. Any remnant remaining in the system is dumped to the waste container 52 through the waste valve 48.

Four operative circumstances help describe the status as depicted in FIG. 1. These will be explained to set the stage for subsequent operative steps which relate to FIG. 2 and so on. In the first instance, the process input line 12 connects to the output line 14. That makes the process sample available, but it is really not delivered at that point in time. Rather, it just flows through the equipment. Secondly, the loop 20 for the additive is filled. It is filled and this flow continues indefinitely so that there are no bubbles caught in the additive loop 20. Flow continues in FIG. 1 from the left to the right for the additive as it does for the process sample.

As configured in FIG. 1, flow continues with the wash water from the source 18 through the valve 38, the valve 15, thereby proceeding into the valve 15 at the port 15-4 and back out via the sample loop 16, and then down through the mix line 40. It continues to flow through the mixing loop 44, and out through the waste valve 48 and to the waste container 52. This can be wash water in the instance that water is an acceptable wash material. It can also be an organic solvent if that is required. Thus, the washing process clears the sample loop 16; in addition, it clears the mixing loop 44 and its cylinder 46.

Figure 2:
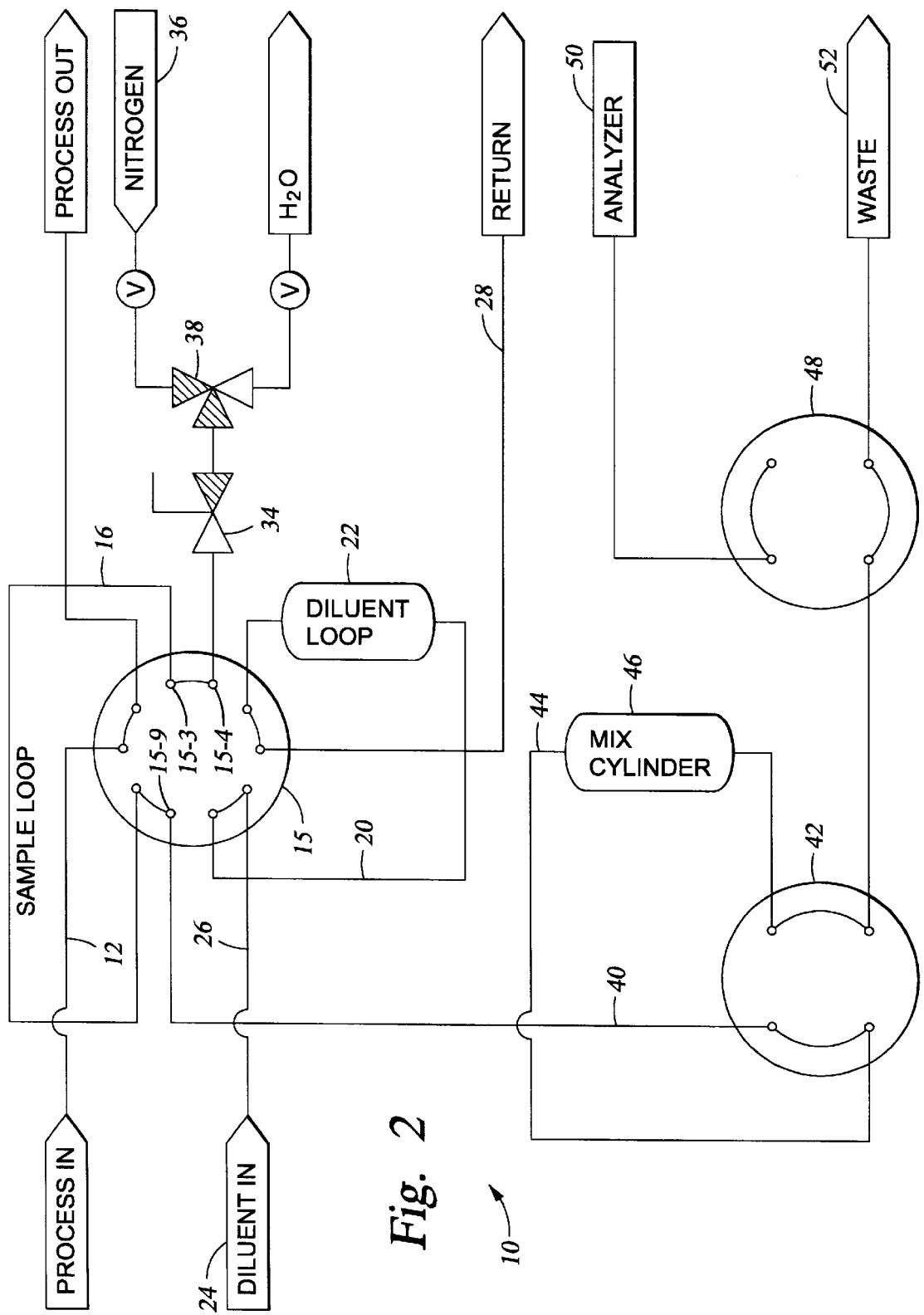

Attention is now shifted FIG. 2 of the drawings. The valve 38 is operated so that the gas is delivered from the gas source 36. Nitrogen is the preferred gas because of cost. The valve 42 is reversed. Gas now flows to clear the lines. This flows for a selected interval. This will dry the lines. When they are blown dry, the lines exposed to the sample and additive are then cleared.

In summation, the deployment of the equipment as illustrated in FIG. 1 is continued indefinitely. Finally, it is terminated and the switched valve 38 then delivers the drying gas. That gas again is vented to the waste container 52. That can be vented atmosphere because it is nitrogen.

Figure 3:
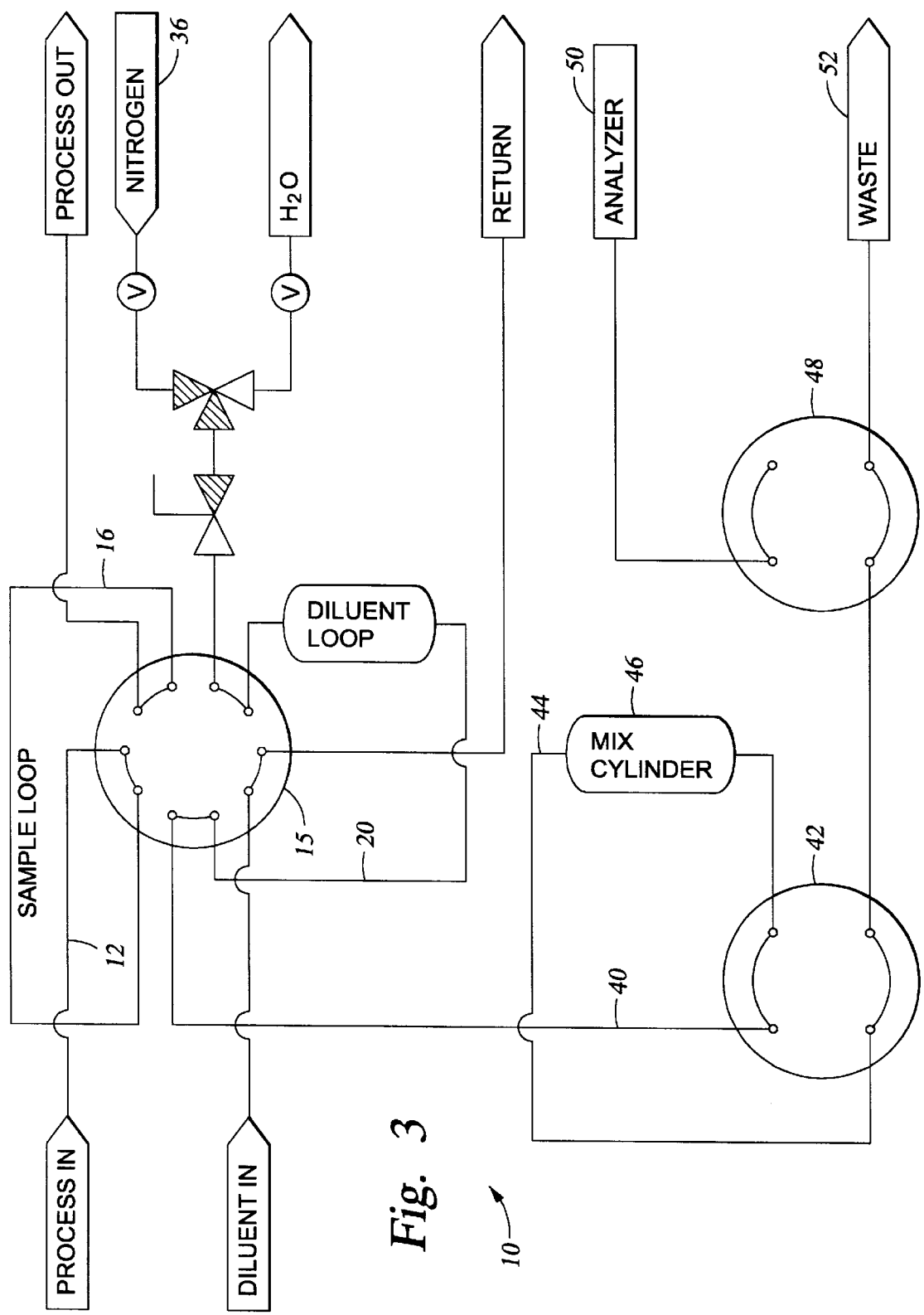

FIG. 3 illustrates a change in the operative connection. The valve 15 has been operated in FIG. 3. Note that the sample loop 16 is now operatively connected with the process sample source. Sample flows through the line 12 and fills the sample loop 16. This process may continue for a few seconds or for a long time. The step shown in FIG. 3 which involves operation of the control valve 15 is carried out during continuous flow of the drying gas. Thus, two changes are implemented in comparison of FIG. 3 with FIG. 2 and are rotation of the valve 15 and the valve 42. The valve 15 enables filling the sample loop 16 while still drying a portion of the equipment with the gas from the nitrogen source 36. As shown in FIG. 3, the drying gas sweeps the loop 20 of additive and clears that loop. As a result of the operation of the valve 15, FIG. 3 illustrates gas flow from the gas source 36 into the loop 20. This drying gas still passes through the mixing valve 42 and into the loop 44. It is still delivered through the waste valve 48 to the waste container 52, bearing in mind that the waste container 52 typically is not a sealed container capable of confining the gas. If the gas has great value, it might be desirable to capture it by making the container 52 into a sealed container. A pressure regulator and output pump may be necessary to control filling of the container 52 and to maintain a stabilized back pressure through the waste valve 48.

To summarize the operative condition in FIG. 3, the sample loop 16 is filled, the additive loop 20 is dried after emptying while, additive in the loop 20 is expelled from the loop 20 by the gas flow and is directed to the mixing chamber 46. The additive is delivered first. The additive is waiting for the sample which will be delivered in the next step. The additive in the cylinder 46 will fill it to a level depending on the flow of additive.

Figure 4:
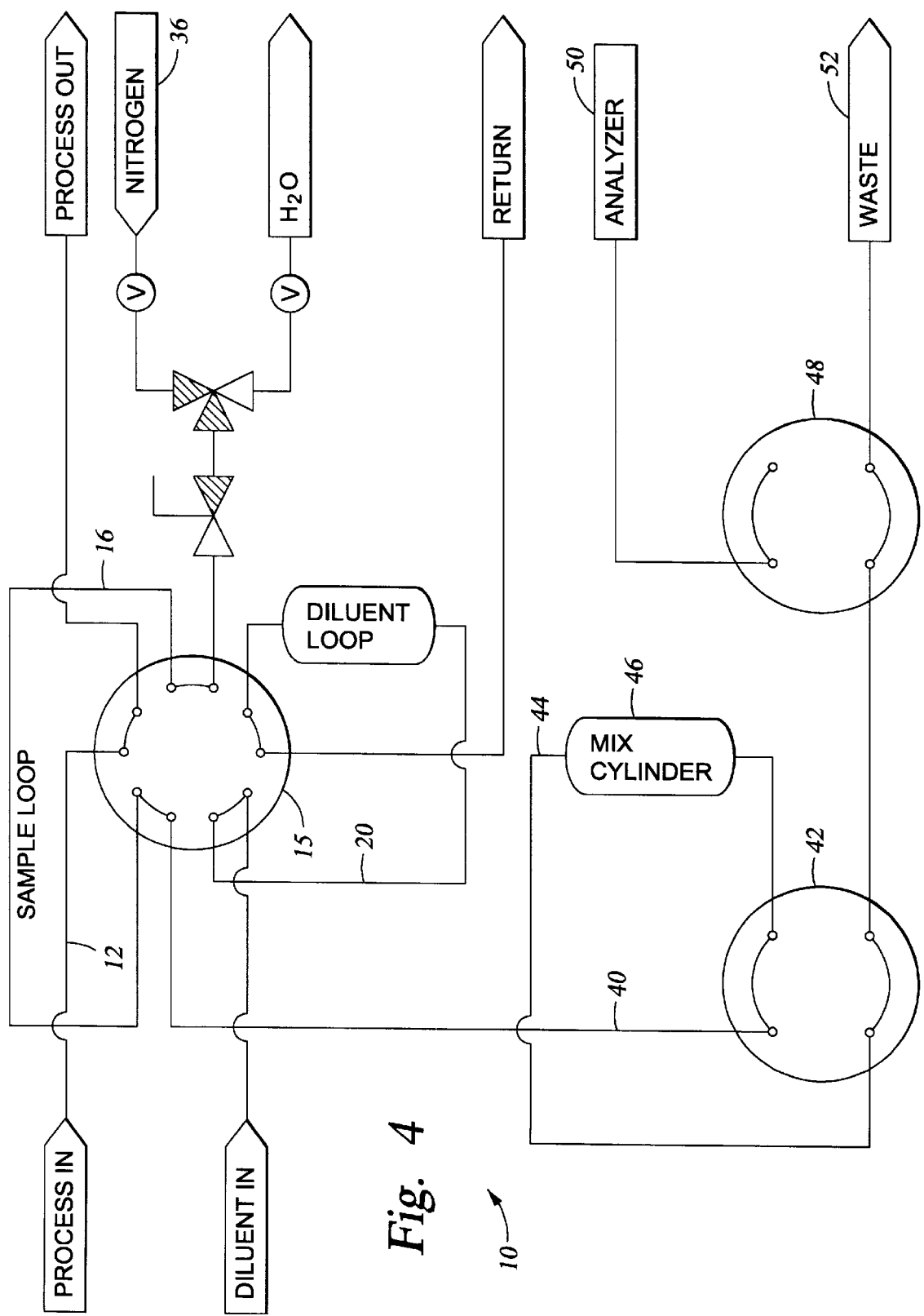

Going now to FIG. 4 of the drawings, the control valve 15 is switched and restored to the position achieved originally in FIG. 1 of the drawings. There is one notable difference. The process is now disconnected or bypassed. The sample loop 16, having been filled in the step associated with FIG. 3, holds a measured quantity of sample which is now pumped out by delivery of the flowing nitrogen. It pushes the sample out of the loop 16, and delivers it through the mix line 40 to flow into the mixing loop 44. It bubbles up into the cylinder 46 and is commingled with the additive which is there. That enables bubbling into the liquid already in the chamber. Interestingly, mixing occurs in the mixing loop 44. Substantially all the mixing, however, occurs in the chamber 46. When liquids are delivered they tend to flow through the capillary lines in droplets or a solid stream. Liquid is pushed from the sample loop 16 and is delivered by the drying gas. In effect, all the liquids accumulate in the chamber 46 and are captured at that location. Effectively, the sample is added into the additive. By delivering in this sequence, the sample, sometimes smaller in volume than the additive, is commingled with it by bubbling up from the bottom. It is driven by the gas flow and therefore is agitated or stirred by the bubble flow. While this occurs in the mixing loop 44, the rest of the equipment is substantially devoid of any remnants in the form of droplets clinging to the wall of the lines.

Figure 5:
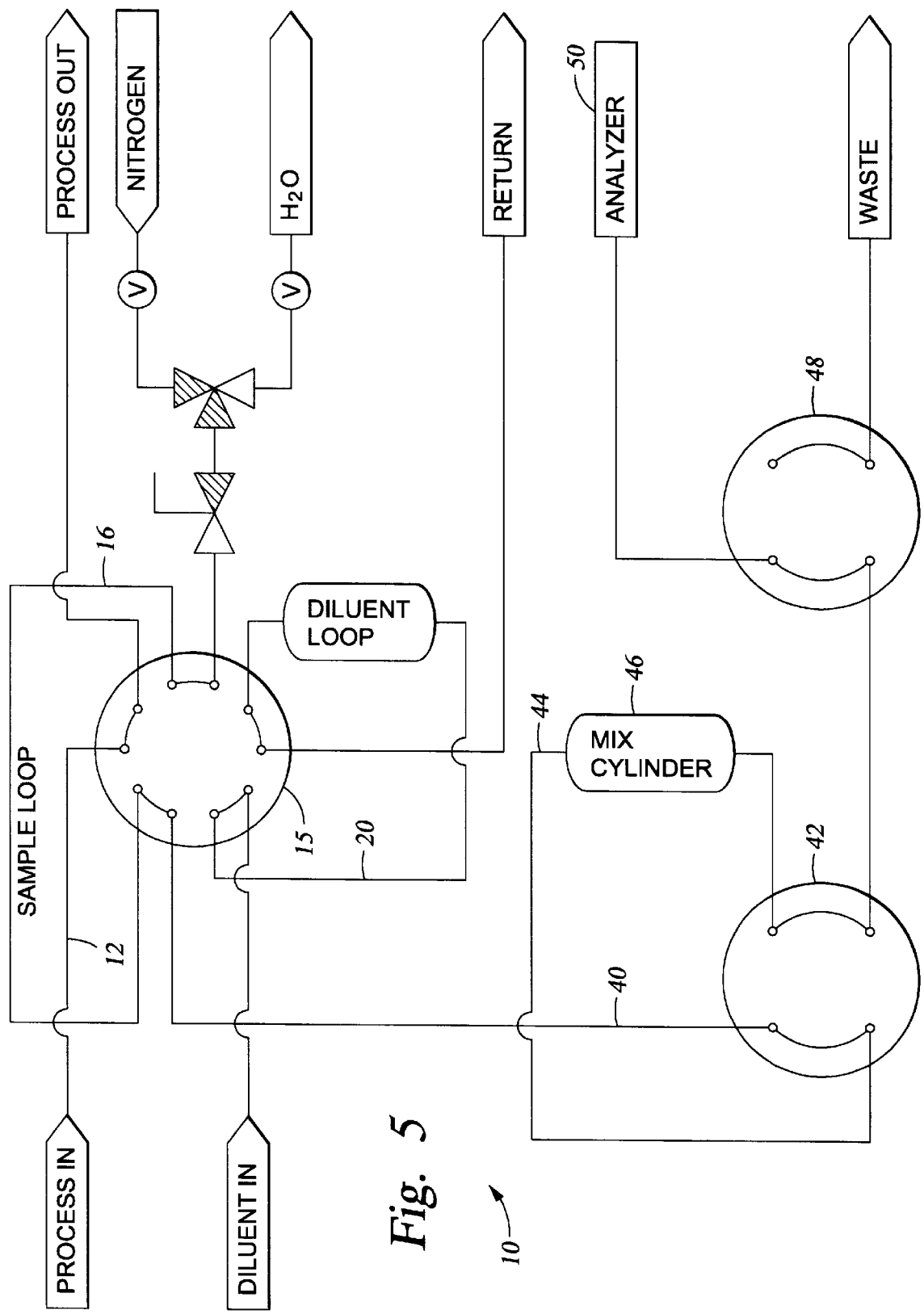

Attention is now directed to FIG. 5 of the drawings. In this view, it is assumed that sufficient time has passed so that the bubbles of gas flowing through the mixing cylinder 46 have thoroughly mixed the additive and sample. Moreover, the flow at this time is sufficient that the thorough agitation completes mixing in this cylinder 46. FIG. 5 shows that the nitrogen flow is continued through the control valve 15, the sample loop and down through the mixing line. FIG. 5, however, shows the valve 42 operated. When it is operated, the nitrogen gas is introduced into the cylinder 46 from the top and the liquid is forced down and out of the cylinder 46. It is delivered through the mixing valve 42 and the waste valve 48. This delivers the sample with the additive to the analyzer 50. The physical relationship of all the components should be noted. In general terms, all the components in the apparatus 10 can be arranged in any relative relationship. It is, however, desirable that the cylinder 46 be liquid filled from the bottom, while the nitrogen gas is introduced from the top to force the accumulated liquid down and out of the cylinder 48. In that sense, the cylinder is positioned as shown in these drawing in a physical sense. It is positioned upright to assure voiding of liquid.

Alternative Embodiment

Figure 6:
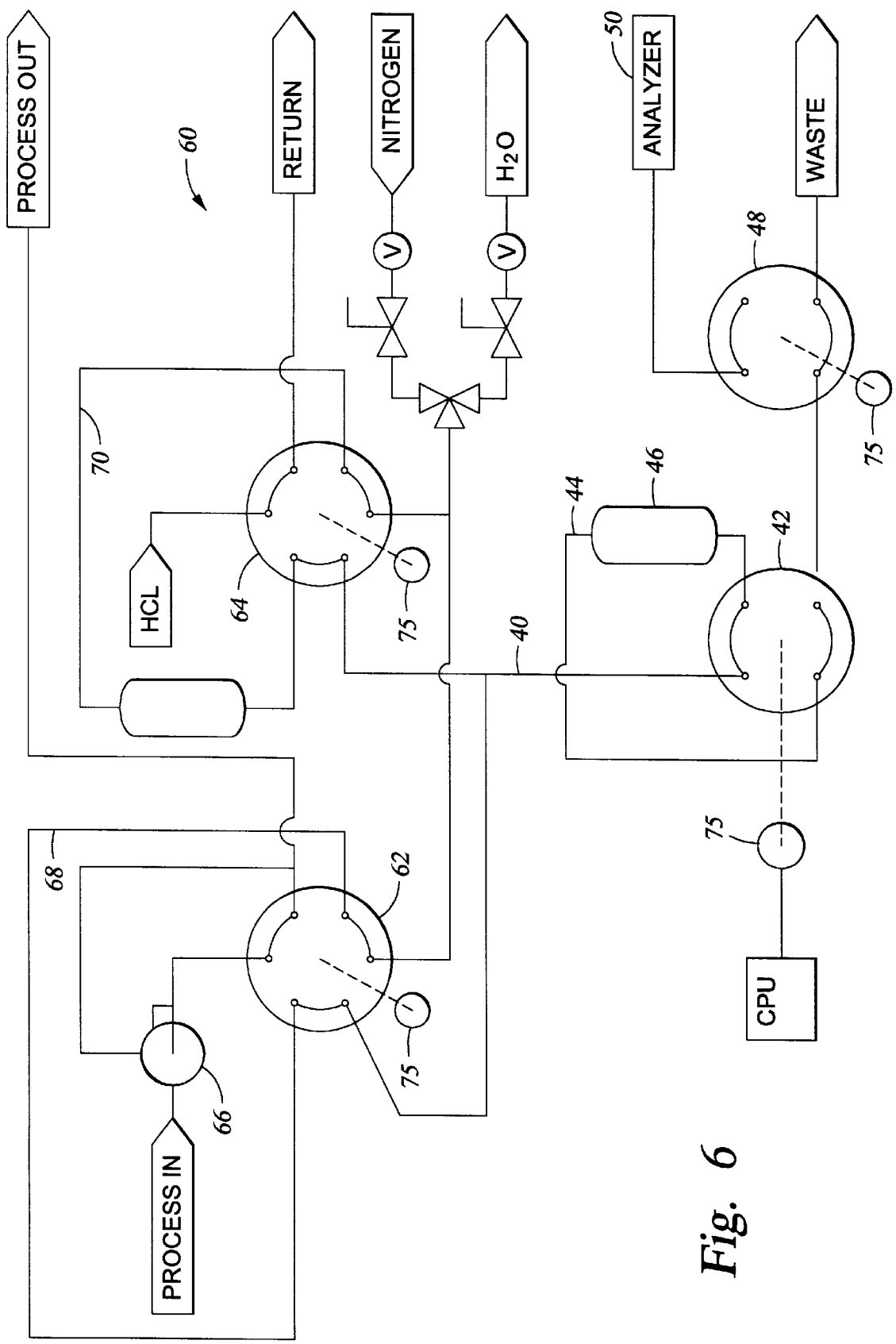
FIG. 6 shows an alternative form utilizing two separate six port, dual position valves in the valve control system which otherwise functions in a similar fashion to the structure shown in the other views.

Attention is now directed to FIG. 6 of the drawings. The control valve system shown in FIG. 1 utilizes a ten port, two position valve. This kind of valve is readily available from Valco Instruments Company, Inc., Houston, Tex. They also vend six port, two position valves. FIG. 6 shows an alternative arrangement. This alternative arrangement connects the two valves in a different way. Nevertheless, the two valves still include the equipment necessary to operate in the same mode. More specifically, the arrangement of the equipment shown in FIG. 6 sets out an alternate embodiment 60 which utilizes a process control valve 62 and an additive control valve 64. Going to the first valve, it connects with a process through an optional filter 66 and then fills the loop 68. The loop 68 corresponds to the sample loop 16 shown in FIG. 1 of the drawings. The additive control valve 64 controls the input of the additive to fill the additive loop 70, and that loop corresponds to the additive loop 20 shown in FIG. 1. Wash water and nitrogen are input in the same fashion as before from the same type sources. These inputs are protected by check valves at the input stage. The output of the two valves 62 and 64 is summed at a mixing line 40. The mixing line 40 has two separate inputs which enable the mixing line to deliver the additive and the sample. They are delivered through the mixing valve 42 as before and are then delivered to waste through that same valve 48. The system still includes the analyzer 50.

The embodiment shown in FIG. 6 is operated to fill the loops 68 and 70. This provides the measured quantities needed for operation. In addition, they are filled to the measured quantities to achieve the desired ratios. The ratios again are selected and controlled by choice of loop capacities. The loops are made small or large as required and they achieve a desired ratio such as a mixing ratio of 10:1, 100:1 and so on. The two loops are then delivered to the mixing line 40 so that the mixing loop 44 is again filled in the same fashion. The mixing loop again includes the mixing container 46. It is preferably held in a physically oriented position so that it is filled from the bottom and subsequently drained from the bottom as before. One difference is that the two loops 68 and 70 can be emptied through the mixing line 40 in the same sequence, or in the reverse sequence. There may be reasons peculiar to a particular process requiring that the contents be delivered in the same or in the reverse sequence. Operation of the valves 42 and 48 in FIG. 6 is done in the same manner. Preferably, all of the valves 42, 48, 62 and 64 are operated by suitable controllers 75 operated in timed sequence by a master timer having a CPU to operate the equipment.

EMULSIFICATION ANALYSIS

Figure 7:
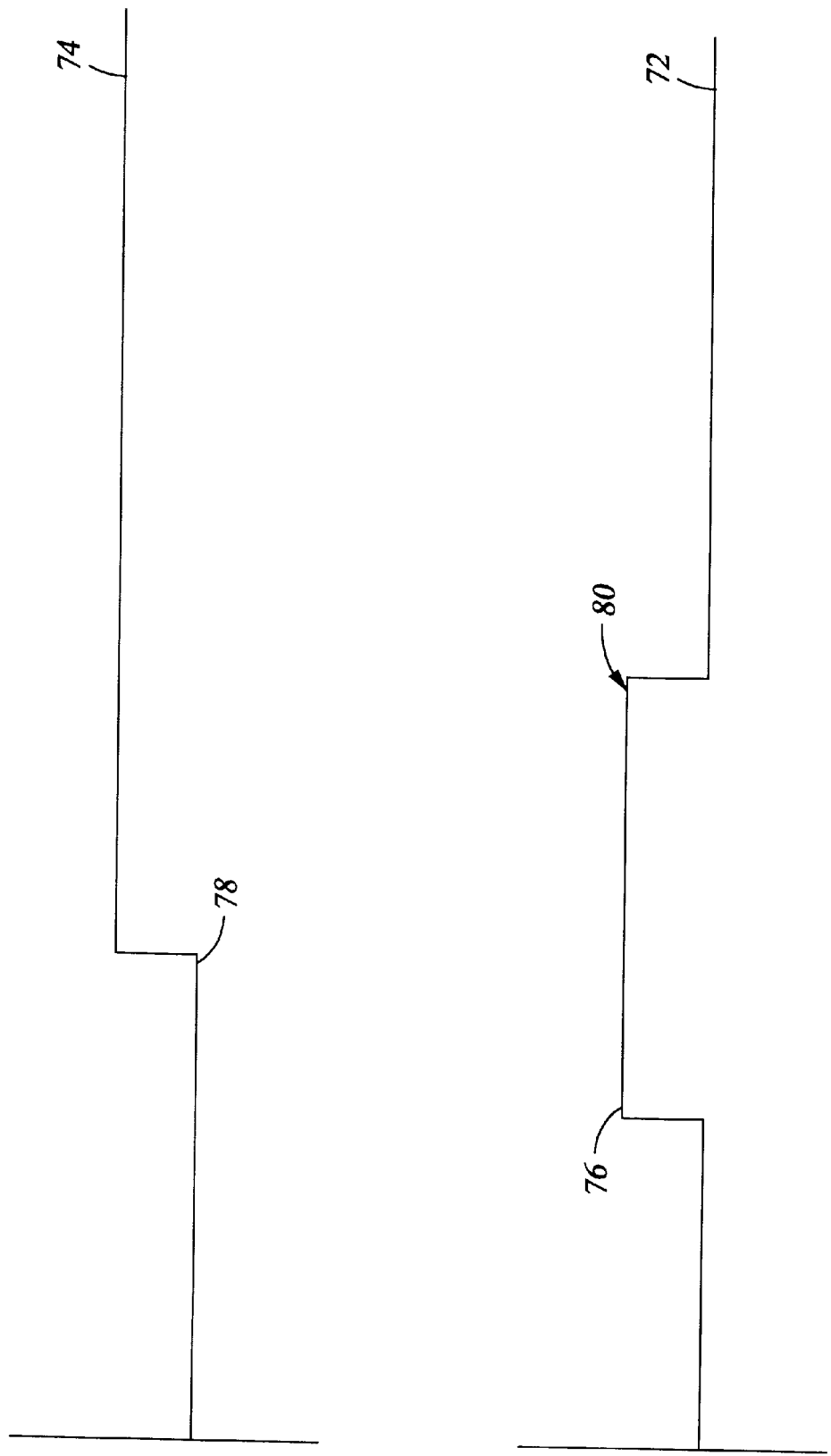
FIG. 7 is an operational timing chart.

At the introduction of the present disclosure, it was noted that some mixtures would be W/W and others would be O/O. There will be occasions where the mixture is O/W or W/O. An example will make this more clear. Sometimes, the chemistry of the transaction permits the oil and water based materials (meaning the sample and the additive) to go into solution at least in some measure. In some instances, they may not do this readily and will simply form an emulsion. The emulsion is formed in the chamber 46. It is stirred and agitated in that chamber to assure suitable emulsification. Thereafter, the equipment is operated to deliver the emulsion. Sometimes, however, after the emulsion is formed it may be desirable to let it sit, permitted time to pass without agitation. If that is the case, the flow of nitrogen gas is stopped. Before that, the nitrogen functions as a drying agent for clearing the lines, and also as a mechanical stirring rod. It stirs the dissimilar liquids in the mixing chamber 46 and will provide the emulsified measured quantity as desired. It may be highly desirable to let that sit so that over time the emulsification will break down. In general terms, the oil in the mixture will rise to the top and the water will settle to the bottom because it is heavier or more dense. FIG. 7 sets forth a timing chart relating to the deliver of this kind of stratified mixture in the container 46. With appropriate time and stratification, the device can be operated to deliver only one, but not the other to the analyzer 50.

Consider as an example the testing of produced petroleum products from one or more wells. The petroleum products typically are oil of different weights which include different measures of water, sand, salt, and the like. In this instance, assume for purposes of disclosure that the production stream includes some sand and salt in the oil. Where that occurs, some of the sand will drop out but some of the salt will remain in the oil. While it is not specifically ionized in solution, it is carried in the flowing oil. This can be oil that is produced from the formation, or it can be a cut of the oil even subsequent to significant processing. For instance, even where the production oil is processed to remove sand and even where it is processed to remove heavier or lighter fractions (e.g. through partial distillation), there will be some salts carried with it. While the most common salt is NaCl, other salts of calcium, potassium, and sodium are carried with oil. Commonly, these salts are chlorides, and they will sometimes include a small measure of sulfates and other less common salts. Suffice, salts sometime pose a problem. Subsequently, in combustion, metal cations in conjunction with the halogen salts thereof can be combusted and thereby create some corrosive combustion gases. Briefly, the halogens (during combustion) create a transitory state in the plasma of highly corrosive halogen atom which will tend to rapidly corrode the exposed metal surfaces in the combustion chamber. In a piston and cylinder context or a turbine blade, metals are attacked by extremely corrosive fluorine and chlorine atoms. It is desirable, therefore, to pull these out. They have to be measured first to know the amount of additives necessary to remove the various metal halogen salts in the produced petroleum or the partially processed petroleum, or the various cuts from the produced petroleum. A classic example of this problem includes metal halogen salts in diesel fuel.

To remove the metal halogen salts in diesel fuel, certain additives must be placed in the system. Before that is done, the amount of the metal halogen salts needs to be quantified. It is difficult to measure metal halogens in organic liquids. It is easier to measure the metal halogens in water. That problem is dealt with in this system easily. Assume for this description that the sample is therefore produced petroleum or processed petroleum commonly having a form useful in a diesel engine. It is tested by first mixing to form and oil/water (O/W as denoted herein) emulsion. That is formed by bubbling nitrogen through the chamber 46. Then after thorough mixing to assure contact in the emulsion, it is permitted to sit, and with the passage of time and in the absence of further agitation, the water will stratify in the bottom of the chamber 46. Assume for purposes of discussion that equal portions of oil and water are introduced into the chamber 46. Knowing this derives from the size of the loops for the sample and for the additive, the valves 42 and 48 are operating in a timed sequence to assure deliver of the sample so that metal halogen salts can then be measured. Assume for purposes of description that the sample loop holds 100 milliliters of the oil suspected to have metal halogens therein. The additive loop is also used to store 100 milliliters of water. Ultimately, the two are thoroughly mixed in the chamber 46 and then permitted to stratify. After waiting an appropriate timed interval, the valve 48 is then operated. FIG. 7 shows the curve 72 descriptive of its operative status. The curve 74 shows the operative status of the valve 42. As illustrated using FIG. 6 as an example, the valve 48 is connected to the waste receptacle. It is switched at the transition 76 shown in FIG. 7. That then directs the flow to the analyzer 50. A fraction of a second after the valve 48 is operated, the valve 42 is then operated. It is switched from the connection shown in FIG. 6 at the instant 78. This then connects the valves 42 and 48 so that the stratified liquid in the chamber 48 is removed from the bottom and delivered to the analyzer 50. Because of stratification, the first outflow is water. Having been agitated with intimate contact between the oil and water, a substantial portion of the metal halogen salts in the oil transfer into the water. While beginning with pure water, the salts in the oil are transferred into the water, and the water is transferred out beginning at the instant 78. Assume that the mixing container 46 includes the 200 milliliters of stratified liquid resulting from using sample loops of 100 milliliter size, the delivery rate can be calculated readily to empty the 200 milliliters in the container 46. The valve 48 is operated just before the valve 42 is operated, and then the valve 48 is switched off at the instant 80. This assures that the first part of the operative interval 74 shown in FIG. 7 will deliver first the water, and then the oil, but the oil is switched to assure that it is delivered away from the analyzer. In effect, the analyzer is provided only with the water and anything carried in the water. This not only makes a transfer of the metal halogen salts in the oil over to the water, it quarantines and isolates the water for subsequent testing free of the oil. In general terms, it is much easier for the analyzer 50 to measure the metal halogens in the water. It is possible to test either the metal or the halogen. It is preferable and easier to do so by testing the halogen content. Analyzers for measurement of fluorine and chlorine content in the water are believed to be readily known. If need be, they can be analyzed through a mass spectrometer, but that is a relatively expensive device. There are less costly test instruments which can provide a good reading. If need be, the metal components of the salts can also be measured.

The foregoing process exemplifies one method of removing metal halogen salts. It will also work for other salts such as sulfates, nitrates, and a fairly long list of comparable salts. This is especially true of the salts which are commonly recovered from oil well production. It is also true for salts which are carried along even though the produced oil is subsequently, partially, or substantially processed and also is effective for the various distilled cuts of produced oil. For instance, lighter cuts such as gasoline, jet fuel, and even diesel fuel can be tested with this process.

While the foregoing is directed to the preferred embodiments of the invention, the scope of the invention is determined by the claims that follow.

What is claimed is:

1. A sampling system comprising a sample source containing a measured sample, and further comprising:
   (a) a switched sample measuring container controllably switched so that said measured sample is obtained therein from said sample source;
   (b) an additive measuring container having an input from a supply of a sample additive wherein said additive measuring container holds a measured size sample additive,
   (c) wherein said sample and sample additive are measured to a specified ratio and said ratio is dependent on the relative sizes of said measured sample and sample additive;
   (d) a mixing chamber connected to said sample measuring container and said additive measuring container to receive said measured quantities;
   (e) control valves connected to said sample measuring container and said additive measuring container to control transfer into said mixing chamber;
   (f) an outlet connected to said mixing chamber for delivery after mixing of said sample and said additive; and
   (g) wherein said sample measuring container comprises a measured sample loop having two ends and a calculated capacity, and said loop is connected to two ports of a multiport control valve.

2. The apparatus of claim 1 wherein said additive measuring container comprises a measured sample loop having two ends and a calculated capacity, and said loop is connected to two ports of said multiport control valve.

3. The apparatus of claim 1 wherein said control valves comprise a multiport two position rotatable valve having two ports thereof connected with said sample measuring container for controlling filling of said sample measuring container, and having two ports connected with said additive measuring container for controlling filling of said additive measuring container.

4. The apparatus of claim 3 including a rotatable valve controller.

5. The apparatus of claim 1 wherein said mixing chamber is connected through a mixing valve to receive the measured sample from said sample measuring container and to receive the additive from the additive measuring container.

6. The apparatus of claim 5 wherein said mixing valve has two ports connected to a mixing loop and said loop is sufficiently large to receive said sample and additive therein.

7. The apparatus of claim 1 wherein said control valves include a multiport, two position, rotatively operated valve switching between two positions, and wherein said valve has ports controlling the flow of sample and separately controlling the flow of said additive to enable said sample and additive to be input to and later removed from said containers.

8. The apparatus of claim 7 including a single 10 port rotatively operated valve for sampling said sample measuring container and said additive measuring container.

9. The apparatus of claim 8 wherein said valve controls wash flow into said valve for said sample measuring container and said additive measuring container.

10. The apparatus of claim 1 wherein said mixing chamber comprises a container connected in a loop having two ends, wherein the two ends of the loop are connected to a mixing valve for control of mixing therein and said mixing container receives and holds the sample and additive therein after transfer thereto.

11. The apparatus of claim 1 including a wash solution source connected to said control valves to provide wash solution to said valves to controllably wash said sampling system.

12. The apparatus of claim 1 including source connected by said control valves to said sample measuring container to direct a fluid flow through said container to clear said sample measure container.

13. The apparatus of claim 1 including source connected by said control valves to said additive measuring container to direct a fluid flow through said container to clear said additive measuring container.

14. The apparatus of claim 12 wherein said source is a wash liquid.

15. The apparatus of claim 13 wherein said source is a wash liquid.

16. The apparatus of claim 12 wherein said source is a drying gas.

17. The apparatus of claim 13 wherein said source is a drying gas.

18. The apparatus of claim 17 wherein said source also includes a wash liquid.

19. A method of obtaining a sample comprising the steps of:
   (a) placing a measured sample in a sample measuring container of a first volume;
   (b) placing a measured sample additive in an additive measuring container of a second volume;
   (c) filling said sample measuring container with said measured sample and filling, said additive measuring container with said measured sample additive thereby forming a ratio of measured sample to measured sample additive defined by said first and said second volumes;
   (d) sending the measured sample and the measured sample additive in said ratio to a mixing container; and
   (e) mixing the sample and additive in the mixing container.

* * * * *

UNITED STATES PATENT AND TRADEMARK OFFICE
CERTIFICATE OF CORRECTION

PATENT NO. : 6,324,924 B1
DATED : December 4, 2001
INVENTOR(S) : R. Peterson

It is certified that error appears in the above-identified patent and that said Letters Patent is hereby corrected as shown below:

Column 1,
Line 24, please change "represent" to -- represents --.
Line 25, please change "unsoluable" to -- insoluble --.

Column 2,
Line 22, please change "extend" to -- extent --.
Line 29, please add a comma after "solution" and before "they".
Line 30, please delete the space between "down" and "stream" to make "downstream".

Column 3,
Line 1, please make "shows" read -- show --.

Column 5,
Line 48, please add -- into the -- after "vented".

Column 6,
Line 54, please make a new paragraph starting with "The physical relationship".
Line 60, change "cylinder 48" to -- valve 48 --.
Line 61, please make "drawing" read -- drawings --.

Column 7,
Line 60, please change "permitted" to -- and permit --.

Column 8,
Line 3, please change "deliver" to -- delivery --.
Line 30, please change "atom" to -- atoms --.
Line 49, delete the word "and" after "form".
Line 59, please change "deliver" to -- delivery --.

UNITED STATES PATENT AND TRADEMARK OFFICE
CERTIFICATE OF CORRECTION

PATENT NO.    : 6,324,924 B1
DATED         : December 4, 2001
INVENTOR(S)   : R. Peterson It is certified that error appears in the above-identified patent and that said Letters Patent is hereby corrected as shown below:

Column 9,
Line 63, please change "additive," to -- additive; --.

Column 12,
Line 2, please delete the comma after "and filling".

Signed and Sealed this

Seventeenth Day of September, 2002

Attest:

JAMES E. ROGAN
Attesting Officer    Director of the United States Patent and Trademark Office